(12) United States Patent
King et al.

(10) Patent No.: US 6,339,075 B1
(45) Date of Patent: *Jan. 15, 2002

(54) USE OF DEXTRAN AND OTHER POLYSACCHARIDES TO IMPROVE MUCUS CLEARANCE

(75) Inventors: Malcolm King, Edmonton; David P Speert, Vancouver, both of (CA)

(73) Assignees: The University of British Columbia, Vancouver; The University of Alberta, Alberta, both of (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/052,614

(22) Filed: Mar. 31, 1998

(30) Foreign Application Priority Data

Jun. 30, 1997 (CA) ............................................. 2209342

(51) Int. Cl.[7] ............................................. A61K 31/00
(52) U.S. Cl. ......................................... 514/59; 536/112
(58) Field of Search ............................. 514/59; 536/112

(56) References Cited

U.S. PATENT DOCUMENTS 5,514,665 A  5/1996 Speert et al. .................. 514/53

FOREIGN PATENT DOCUMENTS

| WO | WO 91 15216 | 10/1991 |
| WO | WO 95 17898 | 7/1995 |
| WO | WO 95/22993 | 8/1995 |
| WO | WO 95/28944 | 11/1995 |

OTHER PUBLICATIONS

"Carbohydrates in Food", edited by Ann–Charlotte Eliasson, published by Marcel–Dekker, Inc., pp. 366–372, 1996.*
Modig, J. *Critical Care Medicine*, vol. 14(5): 454–457, May 1987.*
Modig, J. *Resuscitation*, vol. 10(4): 219–226, Aug. 1983.*
Timsit et al. *C. R. Seances Soc. Biol. Fil*, vol. 165(2): 268–273, 1971.*
De Belder, Anthony. "Medical Applications of Dextran and It's Derivatives", *Polysacc. in Med. Appl.*, ed. Severian Dumitriu publ. Marcel Dekker, pp. 505–523, 1996.*
Wills et al. "Sodium Chloride Increases the Ciliary Transportability of Cystic Fibrosis and Bronchiectasis Sputum on the Mucus–depleted Bovine Trachea" (J. Clin. Invest. 1997; 99: 9–13).
Abstract by Daviskas et al "Interventions Which Increase Mucociliary Clearance (MCC) in Asthmatic and Healthy Subjects", Feb. 1997.
Barghouthi et al "Inhibition by Dextran of *Pseudomonas aeruginosa* Adherence to Epithelial Cells", Am J Respir Crit Care Med 1996; 154: 1788–1793.
W. Feng et al.: "Improved clearability of cystic fibrosis sputum with dextran treatment" Clin. Invest. Med, vol. 20, No. 4 suppl., 1997, p. S99.
W. Feng et al.: "Improved clearability of cystic fibrosis sputum with dextran treatment in vitro" Am. J. Respir. Crit. Care Med., vol. 157, No. 3, 1998, pp. 710–714.
Beller et al, "Biochemical identification of the mucus of pseudomyxoma peritonel as the basis for mucolytic treatment," *American Journal of Obstetrics and Gynecology*, 155(5):970–973 (1986).

* cited by examiner

*Primary Examiner*—Gary Geist
*Assistant Examiner*—D Khare
(74) *Attorney, Agent, or Firm*—Burns, Doane, Swecker & Mathis, L.L.P.

(57) ABSTRACT

This invention relates to the use of polysaccharide such as dextran to improve mucus clearance. In the present invention, dextran has been shown to reduce viscoelasticity and increase mucus clearability of sputum of cystic fibrosis patients. Dextran also reduced viscoelasticity of healthy dog mucus. The present invention therefore may be used to improve mucus clearance in cystic fibrosis patients and treat other conditions associated with defect in airway mucus clearance including chronic bronchitis, bronchiectasis and bronchial asthma.

23 Claims, 5 Drawing Sheets

USE OF DEXTRAN AND OTHER POLYSACCHARIDES TO IMPROVE MUCUS CLEARANCE

FIELD OF THE INVENTION

This invention relates to a method of improving mucus clearance, and more particularly, the invention relates to the use of a polysaccharide such as dextran to improve mucus clearance.

BACKGROUND OF THE INVENTION

Mucus is a critical component of the primary defense mechanism of the respiratory tract, trapping inhaled particulate and microbial material for removal via the mucociliary system. When this mechanism fails to clear sufficiently, mucus accumulates, and must be coughed up as sputum; otherwise it is retained in the respiratory tract, encouraging colonization by microorganisms, which may lead to chronic lung inflammation and obstruction. In cystic fibrosis (CF), airway mucus obstruction has long been considered the most insidious agent of morbidity and mortality. Therapies designed to thin the airway mucus and improve its clearability continue to be a major focus of attention.

Airway mucus is a complex, viscoelastic gel whose physical properties are important for airway defense. Mucus is a variable mixture of water, mucous glycoproteins, low molecular weight ions, proteins, and lipids. The three-dimensional structure that forms the mucous gel is dependent upon a number of forms of bonding. The main elements include the following: 1) disulfide bonds—these covalent links are mainly intramolecular, and join glycoprotein subunits into extended macromolecular chains known as mucins. 2) Because of their extended size, these mucin polymers readily form entanglements with neighboring macromolecules; these act as time-dependent crosslinks, which are susceptible to mechanical degradation. 3) The sugar units that make up the oligosaccharide side-chains (about 80% of the mucin weight), form hydrogen bonds with complimentary units on neighboring mucins. Although each bond is weak and readily dissociates, the numbers of bond sites make this type of bonding potentially very important. 4) Mucins are also ionized, containing both positively charged amino acid residues as well as negatively charged sugar units, principally sialic acid and sulfated residues. These increase in airway disease in general, and in CF the proportion of sulfated residues is further elevated because of alterations in glycosyl transferase activities within the Golgi apparatus. The ionic interactions between fixed negative charges result in a stiffer, more extended macromolecular conformation, effectively increasing the polymer size and adding to the numbers of entanglements. 5) Added to this in airway diseases characterized by infection and inflammation, especially CF, are the extra networks of high molecular weight DNA and actin filaments released by dying leukocytes, and exopolysaccharides secreted by bacteria.

One of the primary aspects of the current treatment of CF lung disease is aimed at changing the physical properties of pulmonary secretions to improve their clearance from the airways. The most successful therapy in CF, and the only mucoactive agent with proven efficacy, is rhDNase. Treatment with rhDNase is based on the fact that the major factor involved in the elevated viscoelasticity of CF sputum is attributed to the presence of naked DNA released into the airway surface fluid (ASF) from bacteria, neutrophils, and other cellular debris. Enzymatic digestion of these DNA macromolecules effectively decreases mucus viscoelasticity and spinnability and enhances the clearability of airway secretions. Other direct-acting mucolytic treatments, such as N-acetylcysteine derivatives, gelsolin, and hypertonic saline, are effective in vitro in CF, but may not necessarily show clinical efficacy. Indirect mucolysis, such as with inhaled amiloride, which blocks the uptake of salt and water across the airway epithelium, is a strategy aimed at enhancing the degree of hydration and diluting the macromolecular component of the ASF. Combined mucokinetic therapies may aim to address more than one mechanism involved in the control of airway mucus secretion and clearance.

DNase, gelsolin and acetylcysteine derivatives are all similar in action in that they degrade the three-dimensional network by mucolysis, or molecular weight disruption. This tends to preferentially affect the elasticity components of the network (as opposed to viscosity), which in model studies improve cough or airflow clearance more than clearance by ciliary action. Agents that affect ionic charge interactions and hydrogen bonds, on the other hand, are not true mucolytic agents because they alter the crosslink density without reducing polymer chain length, the result of which is common reduction in both elasticity and viscosity, and a preferential improvement in ciliary clearance according to model studies.

Ionic agents such as sodium chloride are believed to be mucoactive by shielding the fixed charges along the macromolecular core of the mucin polymer, making it less stiff and less extended and thus reducing the number of entanglement crosslinks with neighboring macromolecules. Wills et al (J Clin Invest 1997; 99: 9–13) disclose that the degree of crosslink reduction is related to the ionic strength in the range of 0 to 500 mOsm NaCl. Nonionic agents such as sugar have also been suggested to improve mucus clearance by increasing osmolarity. Wills et al (J Clin Invest, supra) disclose that increasing the sputum osmolarity by addition of non-electrolytes such as glucose, mannitol and urea increases the ciliary transportability. PCT publication no. WO 95/22993 published on Aug. 31, 1997 similarly discloses increasing mucociliary clearance by inhalation of a substance capable of altering the osmolarity of airway surface liquid, including sugar. On the other hand, PCT publication no. WO 95/28944 published on Nov. 2, 1995 discloses that non-ionizable material such as glucose are not effective in improving sputum transportability.

Dextran is a bacterial byproduct; the dextran macromolecule consists of end-to-end linked glucan groups. Its primary clinical uses are as a plasma volume expander and as an antithrombotic agent which has antiaggregation effects. Dextran has also been shown to exhibit antiadhesive properties in airway epithelial cells, which may make it of value as an antimicrobial agent in preventing the Pseudomonas infection in CF patients (U.S. Pat. No. 5,514,665 issued May 7, 1996 to Speert et al; Barghouthi et al Am J Respir Crit Care Med 1996; 154: 1788–1793).

It has now been found that dextran decreases mucus viscoelasticity and increases mucociliary clearability. The present invention relates to this unexpected finding that dextran and other polysaccharides may be used to improve mucus clearance.

SUMMARY OF THE INVENTION

In one aspect, this invention relates to a method of improving mucus clearance comprising administering to the respiratory tract of a patient in need of such treatment an effective amount of a polysaccharide.

In another aspect, this invention relates to a method of treating lung disease associated with impaired mucus clearance comprising administering to the respiratory tract of a patient in need of such treatment an effective amount of a polysaccharide.

In yet another aspect, this invention relates to a method of improving mucus clearability in a patient having cystic fibrosis comprising administering to the respiratory tract of said patient in need of such treatment an effective amount of dextran.

Preferably, the molecular weight of polysaccharide administered will be less than about 500,000, and more preferably less than about 250,000.

DETAILED DESCRIPTION OF THE INVENTION

In the present invention, dextran has been shown to reduce viscoelasticity and increase mucociliary clearability of sputum obtained from CF patients in vitro, and the effects were dose dependent. Administration of 4% and 0.4% (w/v) dextran resulted in decreased spinnability and viscoelasticity, and the effects were greater at the higher dextran concentration. The predicted mucociliary clearability and cough clearability improved significantly at both concentrations and no significant dose dependency was observed with these derived parameters. The treatment of one CF patient with dextran resulted in decreased sputum viscosity and increased the predicted mucociliary clearability and cough clearability.

These effects of dextran are not specific to CF lung disease and dextran significantly reduced viscoelasticity of healthy dog mucus both in vitro and in vivo. The present invention is therefore not limited to improving mucus clearability in CF patients and may be used to treat other conditions associated with defect in airway mucus clearance including chronic bronchitis, bronchiectasis, bronchial asthma, mucus retention, mucus hypersecretion, and reduced mucociliary clearance.

The effects of dextran, a neutral polymer, are similar to those of sodium chloride treatment since both forms of treatment reduce sputum viscoelasticity in vitro. However, dextran of the present invention is believed to reduce viscoelasticity by competing for hydrogen bonding sites with other mucus glycoproteins resulting in the substitution, by dextran carbohydrate moieties, of oligosaccharide moieties linked to the high molecular weight mucin peptides that make up the mucus gel. For the lower molecular weight dextran (most preferably in the range of 4000 or less), these new hydrogen bonds are structurally and rheologically ineffective, thus reducing the overall crosslink density. This reduction in the crosslinking of the three dimensional mucus glycoprotein network is believed to improve mucus clearance by ciliary and cough mechanisms.

Dextran may be administered to the respiratory tract in the known manner, including by nebulizer via endotracheal tube, or topically, directly to the mucosa. Dextran may be administered in admixture with a pharmaceutically acceptable diluent or excipient. Acceptable diluents or excipients include sodium chloride or Ringer solution, L-arginine, or lysine and their salts. Preferably, dextran with a molecular weight range of about 360 to 4000 will be administered. Dextran at a final concentration of 4 mg/ml and 40 mg/ml in the respiratory secretion achieves the desired therapeutic effect. The concentration of 4 mg/ml dextran in the respiratory secretion is achievable with aerosol delivery of 80 mg/ml dextran solution, based on model calculations. Dextran may be administered two to three times daily and the frequency will depend upon the individual patient's requirement. Other suitable dosage, frequency and modes of administration will be apparent to one skilled in the art.

The mechanism for the improvement in viscoelasticity with dextran administration is believed to be due to the substitution of dextran moieties in hydrogen bonding sites otherwise occupied by oligosaccharide moieties linked to neighboring high molecular weight peptides. The original intermolecular mucin-mucin bonds contribute to the three-dimensional structure that makes up the mucus gel, while the new mucin-dextran bonds form ineffective crosslinks because of the relatively small length of the dextran polymer. Other polysaccharides with a similar number of hydrogen bonding sites to dextran of the present invention or containing sugar moieties that stereochemically complement the oligosaccharide moieties native to the respiratory tract mucins, including oligomers of galactose and fucose and the amino sugars glucosamine and galactosamine are expected to compete for hydrogen bonding sites in the mucus gel, by forming complementary interaction with the oligosaccharide side chains of mucin macromolecules and thereby reduce the overall crosslink density of the mucus gel. These polysaccharides, at a suitable dosage may be administered in the known manner to patients suffering from conditions associated with defect in the airway mucus clearance, including CF, chronic bronchitis, bronchiectasis and bronchial asthma.

The present invention will be further apparent from the following experiments. Moreover, one skilled in the art can readily appreciate that various modifications can be made to the described embodiments without departing from the scope and spirit of the invention. Such modifications are also intended to be within the scope of the invention.

EXAMPLE 1

Materials and Methods:

Subjects—Sputum samples were obtained by voluntary expectoration from 15 adolescent and young adult patients with CF. The patients were all infected with *Pseudomonas aeruginosa*. None of the patients was under current treatment with rhDNase. Approval to collect and use sputum for this in vitro analysis was obtained from the University of Calgary Research Ethics Board.

Dog mucus was obtained from healthy, anaesthetized dogs from the endotracheal tube cuff. Dextran (USHERDEX 4*) was provided by Polydex Pharmaceuticals Ltd. (Toronto, ON, Canada). USHERDEX 4 has been analyzed by HPLC and contains dextran oligomers from two units (dimer) to 19 units (19-mer). USHERDEX 4 dextran has a molecular weight of range of about 360 to about 4000.

* Trade-mark

Study Design—Protocol A (CF sputum—0.4% dextran):

Seven samples of sputum (0.40 to 0.60 g) were treated as follows:

i) Baseline aliquot (no in vitro treatment), ii) Negative control aliquot, adding 10% vol. Ringer solution and incubating for 30 min. at 37° C.

iii) Application of 10% vol. Ringer's containing 40 mg/mL USHERDEX 4 to give a final concentration of 0.4% (4 mg/mL) in the sputum; the sample was incubated for 30 min. at 37° C.

Protocol B (CF sputum dose-response):

Eight samples of sputum (0.40 to 0.60 g) were treated as follows:

i) Negative control aliquot, adding 10% vol. Ringer solution and incubating for 30 min. at 37° C.

ii) Application of Ringer containing 40 mg/mL USHERDEX 4 to give a final concentration of 0.4% (4 mg/mL) in the sputum.

iii) Application of Ringer containing 400 mg/mL USHERDEX 4 to give a final concentration of 4% (40 mg/mL) in the sputum.

Protocol C (canine tracheal mucus dose-response):

Seven samples of canine tracheal mucus (ca. 0.1 g) were treated as follows:

i) Negative control aliquot, adding 10% vol. Ringer, incubated 30 min. at 37° C.

ii) Application of Ringer containing 40 mg/mL USHERDEX 4 to give a final concentration of 0.4% (4 mg/mL) in the sputum, incubated 30 min. at 37° C.

iii) Application of Ringer containing 400 mg/mL USHERDEX 4 to give a final concentration of 4% (40 mg/mL) in the sputum, incubated 30 min. at 37° C.

Frog palate mucociliary transportability (FMT): This was determined from CF sputum movement on the ciliated, mucus-depleted frog palate, relative to native frog control (rel. vel., FMT, expressed as a fraction). The movement of a 2–5 μL aliquot of CF sputum was timed; 5 measurements of sputum transport rate were taken to minimize measurement variability. FMT was determined only for the samples in protocol A.

Rheological Measurements on CF Sputum: In this in vitro study, two techniques were used to measure the rheological properties of sputum: spinnability by filancemeter and viscoelasticity by magnetic rheometry.

Spinnability is the thread forming ability of mucus under the influence of low amplitude elastic deformation. The spinnability of CF sputum samples was measured using a Filancemeter (SEFAM, Nancy, France), in which a 20 to 30 μL mucus sample is stretched at a distraction velocity of 10 mm/s. An electric signal conducted through the mucus sample is interrupted at the point where the mucus thread is broken. The length of this thread is known as the mucus spinnability (measured in mm). Spinnability was only determined for sputum samples in protocol B.

Viscoelasticity and Clearance Indices: The magnetic microrheometer technique was used to measure the viscosity and elasticity of the sputum samples. A 100 μm steel ball was positioned in a 5–10 μL sample of sputum, and the motion of this sphere under the influence of an electromagnet was used to determine the rheological properties of the sputum. The image of the steel ball was projected via a microscope onto a pair of photocells, whose output was amplified and transmitted to an oscilloscope. By plotting the displacement of the ball against the magnetic driving force, the viscoelastic properties of the mucus were ascertained.

The parameters of mucus viscoelasticity determined were the rigidity index or mechanical impedance, i.e. $G^*$, reported here on a log scale, expressing the vector sum of "viscosity+elasticity". Two derivative parameters—mucociliary clearability index (MCI) and cough clearability index (CCI)—were computed from in vitro relationships. These two indices predict mucus clearability by ciliary and cough mechanisms, respectively, based on the measured rheological properties and observations of clearance from model studies. The respective formulas are as follows:

$$MCI = 1.62 - (0.22 \times \log G^*1) - (0.77 \times \tan \delta 1)$$

$$CCI = 3.44 - (1.07 \times \log G^*100) + (0.89 \times \tan \delta 100)$$

Statistical Analysis—Data from each protocol are presented as mean ±standard deviation (SD) of the mean. To analyze the significance of changes in spinnability, log $G^*$ at 1 rad/s, MCI, and CCI after administration of Ringer control, 0.4% dextran and 4% dextran, the sputum from each patient served as its own control. Equality of means was tested by analysis of variance (ANOVA), post hoc analysis of changes from baseline was determined by the two-tailed, paired t-test and regression. The paired t-test was also used to determine the differences between spinnability and viscoelasticity after different treatments. Regression was used to determine the correlation between spinnability and viscoelasticity. The StatView statistical package (Abacus Concepts, Palo Alto, Calif.) was used to carry out these analyses.

Figure 1A:
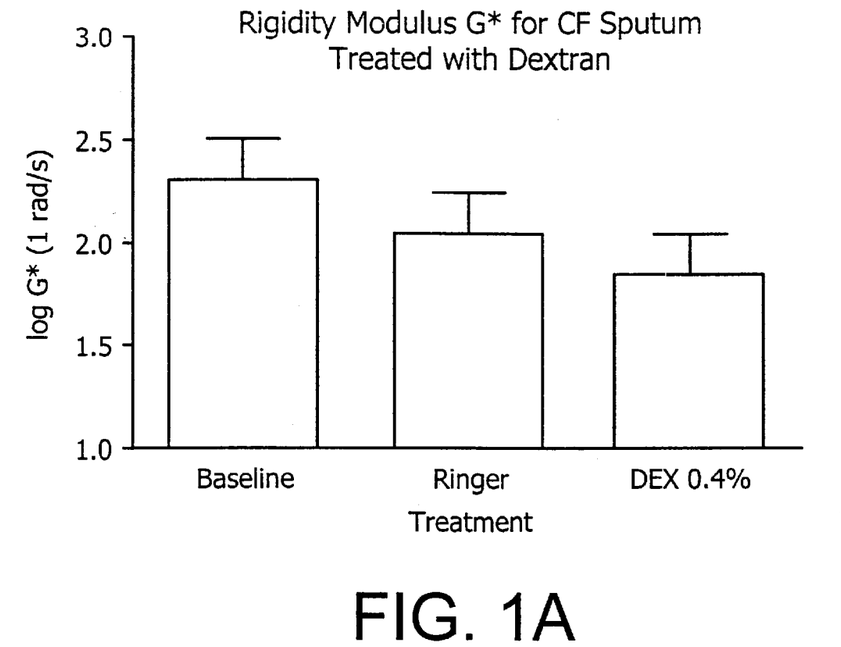
FIG. 1A is a graph showing the effect of dextran treatment on viscoelasticity of sputum samples from CF patients.
Figure 1B:
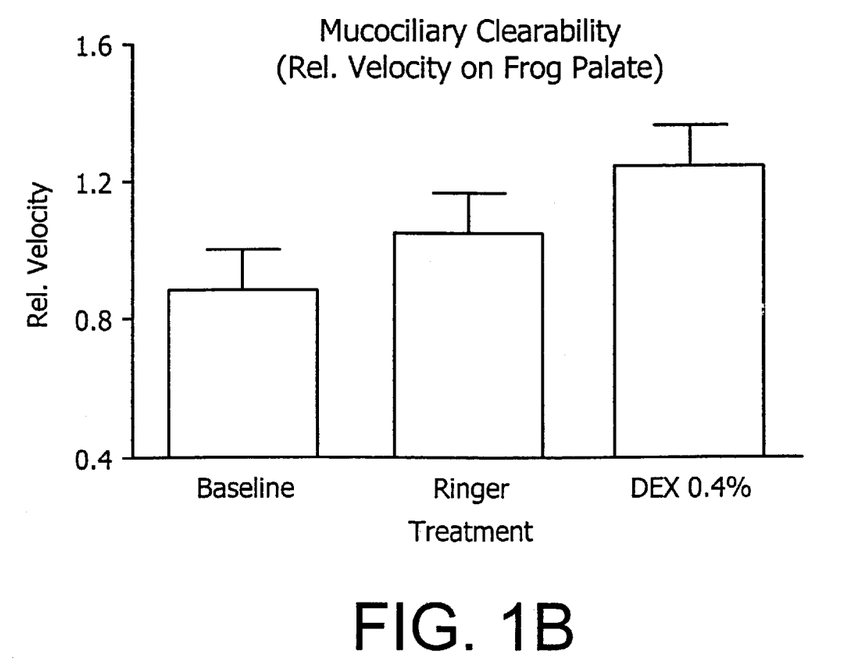
FIG. 1B is a graph showing the effect of dextran treatment on mucociliary clearability of sputum samples from CF patients.

Results:

In protocol A, after administration of 0.4% USHERDEX 4, frog palate mucociliary clearability increased significantly (p=0.046) compared to Ringer control (FIG. 1B). There was a modest dilution effect (reduction in mucus rigidity) associated with the Ringer treatment, and a further reduction due to the Dextran (significant w.r.t. no treatment, p=0.004) (FIG. 1A). Cough clearability (CCI, predicted from rheology) also increased significantly (p=0.019). Mucociliary clearability on frog palate increased more than that predicted from rheology, this extra clearability could be an indication of a surface or antiadhesive effect.

After the initial tests suggested that USHERDEX 4 might have direct, potentially beneficial effects on CF sputum, we conducted further experiments to investigate the dose-dependency of the effects (protocol B) and whether noninfected mucus was also influenced by USHERDEX 4 (protocol C).

Figure 2A:
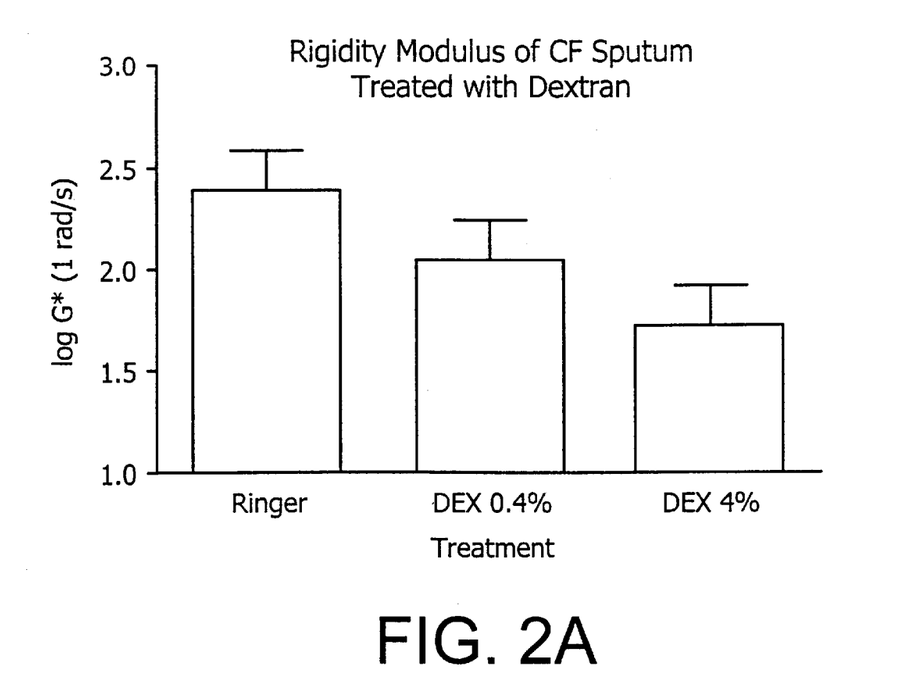
FIG. 2A is a graph showing the effect of 0.4% and 4% (w/v) dextran treatment on viscoelasticity of sputum samples from CF patients.
Figure 2B:
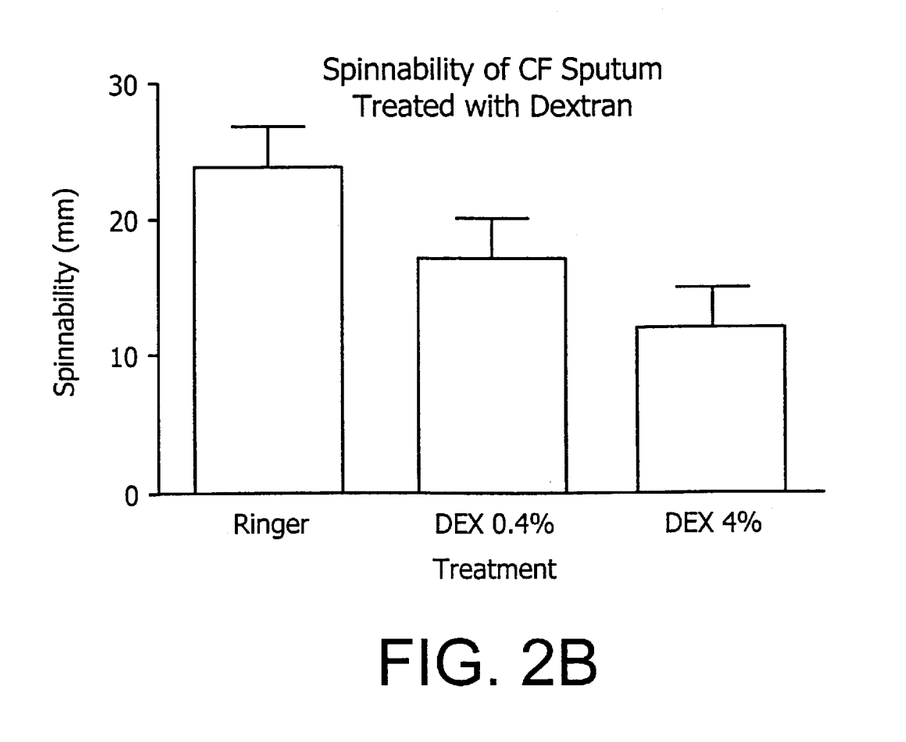
FIG. 2B is a graph showing the effect of 0.4% and 4% (w/v) dextran treatment on spinnability of sputum samples from CF patients.
Figure 3A:
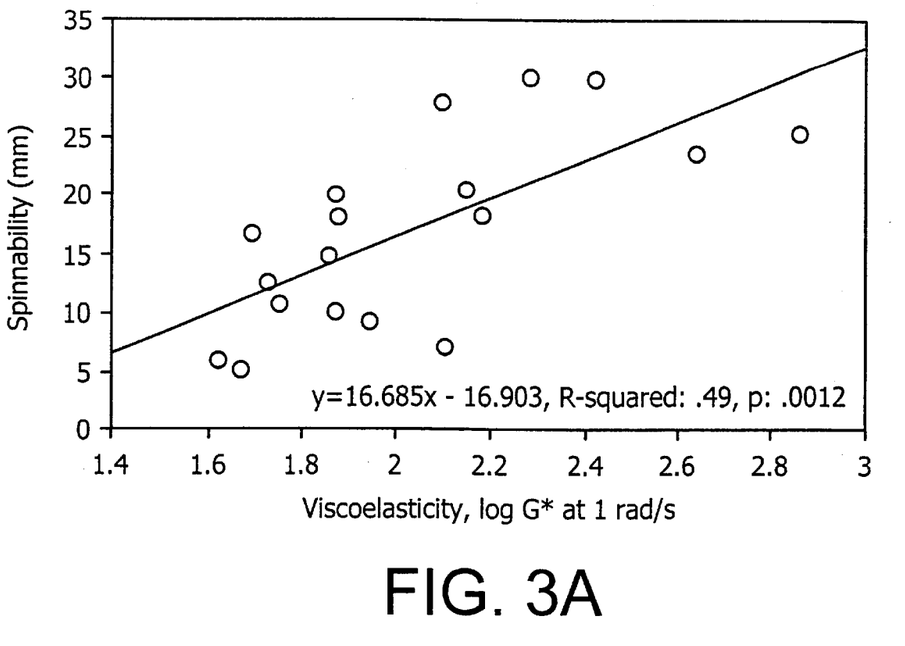
FIG. 3A shows the correlation between spinnability and viscoelasticity.
Figure 3B:
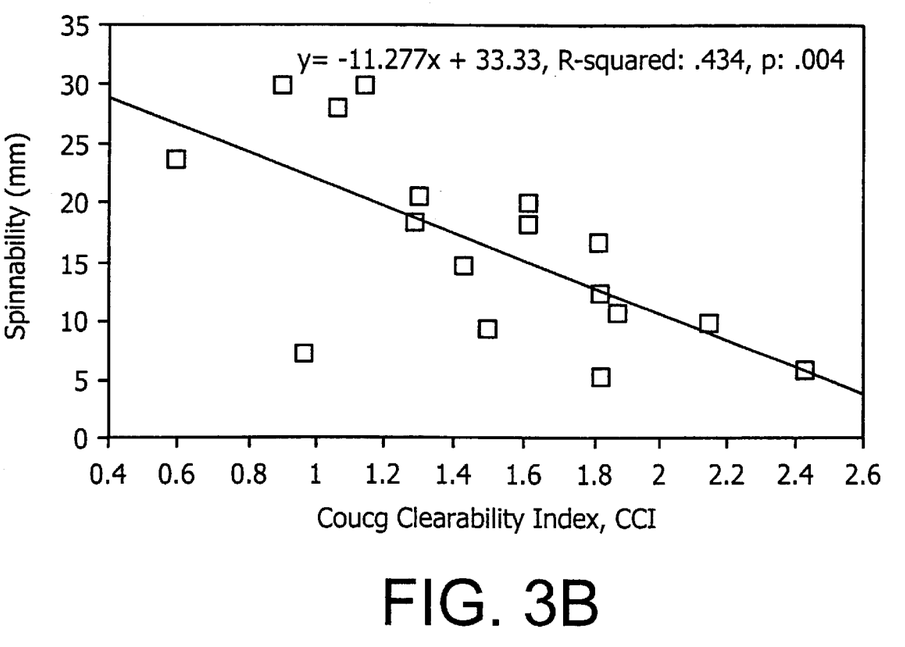
FIG. 3B shows the correlation between spinnability and cough clearability.

In protocol B, compared to saline control, CF sputum spinnability decreased 34.2% by administration of 0.4% dextran (p=0.0121) and 59.8% by administration of 4% dextran (p=0.0016) (FIG. 2B). Furthermore, the reduction in spinnability after 4% dextran was greater than that seen after 0.4% (p=0.0046). At the same time, mucus viscoelasticity (log $G^*1$) was reduced by a factor of 2.43 (0.385 log units) by 0.4% dextran (p=0.0404) and by a factor of 4.57 (0.660 log units) by 4% dextran (p=0.0069) (FIG. 2A). The additional reduction in mucus viscoelasticity observed at the higher dextran concentration was also significant (p=0.0193). Mucociliary clearability (MCI) and cough clearability (CCI) (both predicted from rheology) improved significantly in both treatment groups (MCI: p=0.0252, p=0.003; CCI: p=0.0227, p=0.0423), although no significant dose dependency was seen with these derived parameters. There was a positive relationship between spinnability and viscoelasticity (FIG. 3A), as well as negative correlations between spinnability and predicted mucociliary clearance and cough clearance (FIG. 3B).

Figure 4:
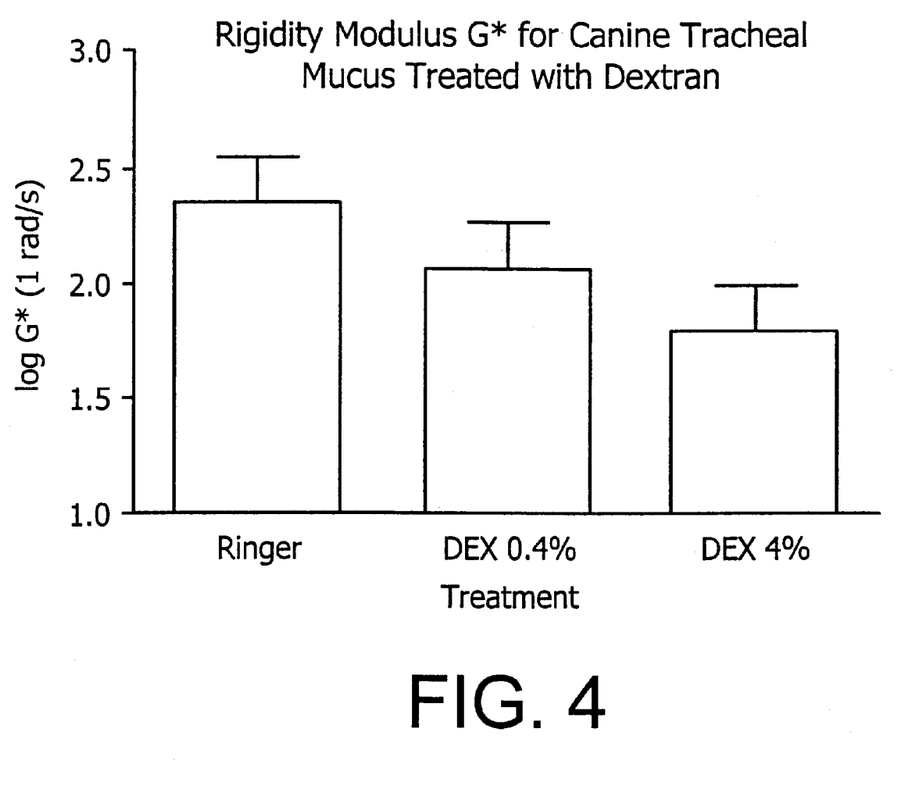
FIG. 4 is a graph showing the effect of 0.4% and 4% (w/v) dextran treatment on viscoelasticity of mucus obtained from healthy dogs.

In protocol C, the viscoelasticity of healthy dog mucus was decreased significantly by treatment with 0.4% dextran (∂ log $G^*$=0.269, p=0.0048) and with 4% dextran (∂ log $G^*$=0.547, p=0.0016) compared to saline control (FIG. 4). Mucociliary clearability (predicted from rheology) only increased significantly for 4% dextran (p=0.0108). Cough clearability (predicted from rheology) increased significantly in both treatment groups (p=0.0385; p=0.0459). The additional reduction in log $G^*$ between 0.4% and 4% dextran treatments did not achieve statistical significance (p=0.09).

Overall, whether for CF sputum or healthy dog mucus, USHERDEX 4 treatment significantly reduced viscoelasticity and increased predicted mucociliary and cough clearability. This effect of dextran was dose dependent, being significantly greater for 4% dextran treatment than for 0.4%. There was no great correlation between frog palate mucus transportability and mucus viscoelasticity, but there was a significant correlation between spinnability and mucus viscoelasticity (p=0.0012), spinnability and mucociliary clearability (p=0.0138), as well as cough clearability (p=0.004) (both predicted from rheology) (FIG. 3).

EXAMPLE 2

Figure 5:
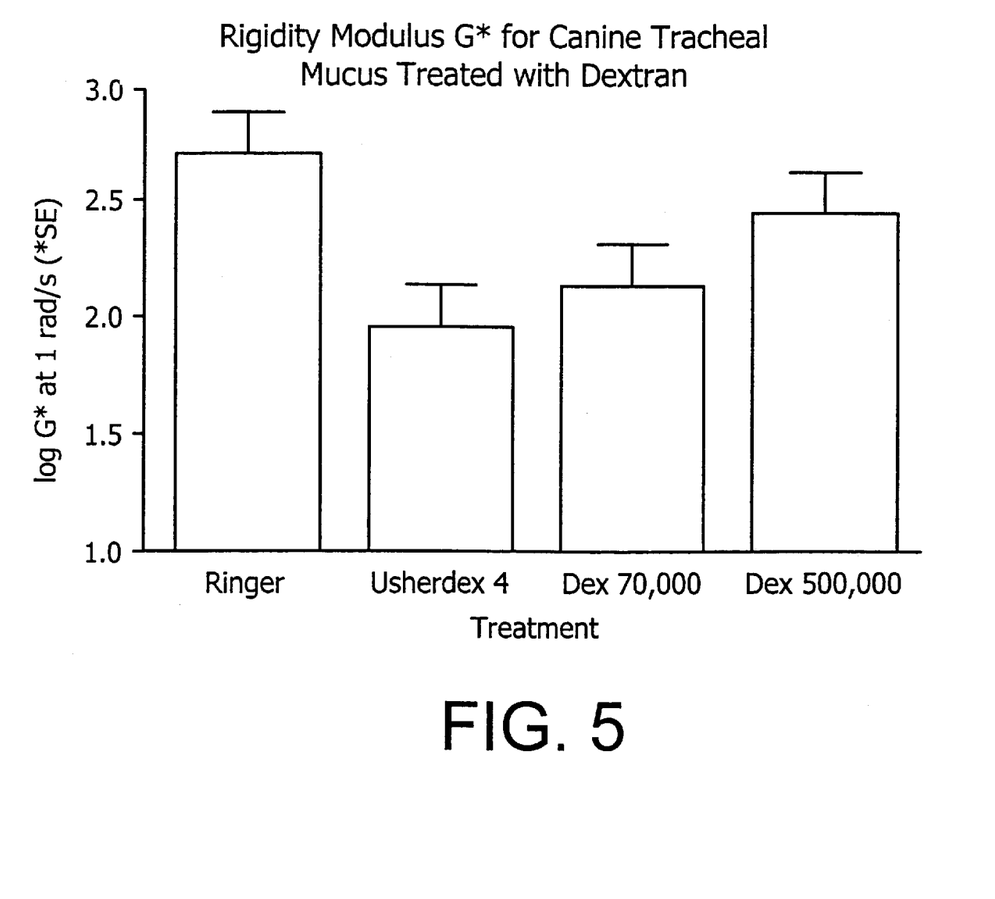
FIG. 5 is a graph showing the effect of different molecular weights of dextran on viscoelasticity of sputum samples from CF patients.

The Effect of Dextran Molecular Weight on CF Sputum Rigidity:
Method:
Sputum samples were obtained from 8 CF patients not receiving rhDNase (Pulmozyme®)—Aliquots of sputum were incubated at 37° for 30 minutes with Ringer diluent (10% added volume) or with three dextrans of different molecular weights, i.e. USHERDEX 4 (average molecular weight of 1800), Dextran 70,000 and Dextran 500,000, to achieve a final concentration of 4% (40 mg/ml). The rigidity modulus (viscoelasticity) was determined by magnetic rheometry.
Results:
The highest molecular weight dextran had no significant effect on mucus viscoelasticity, while the effect of USHERDEX 4 is comparable to that previously shown in Example 1. The intermediate fraction had an intermediate effect (FIG. 5).

EXAMPLE 3

Effects of Dextran on Dog Mucus
Method:
Healthy mongrel dogs were anaesthetized with pentobarbital and intubated. After a 30 min. Ringer aerosol, tracheal mucociliary velocity (TMV by charcoal particle transport) was measured under bronchoscopic control, and mucus for viscoelasticity analysis (magnetic rheometer) was collected by the endotracheal tube method. Then low m. w. dextran (Polydex Pharma., lot #2764, molecular weight range of about 360 to about 4000) in Ringer vehicle was aerosolized to the trachea, followed by the same procedures. We performed 8 expts. in 8 dogs, involving dextran aerosol 30 min administration; all dogs received aerosols of 20 mg/ml, 65 mg/ml, 200 mg/ml dextran.
Results:
Compared with Ringer control, TMV increased to 145% of control (p=0.0417) at 65 mg/ml dextran. There was only a modest increase in TMV at 20 mg/ml and a decrease in TMV with 200 mg/ml dextran. Mucus viscoelasticity significantly decreased to 35% of control (0.452 log units, p=0.0426) at 65 mg/ml. These in vivo data support in vitro findings, that low molecular weight dextran deceases mucus viscoelasticity and increases mucociliary clearance.

EXAMPLE 4

Interaction of Dextran with L-Arginine on Tracheal Mucus Secretion and Clearance in Dogs
Method:
Arginine/arg. HCl was prepared as described by Solomons (Pediatrics 1971;47:384), making a stock solution of 290 mOsm, pH 7.4. Two dilutions were prepared, 97 and 29 mOsm, the balance being Ringers. The solutions were delivered by Pari jet nebulizer to 8 healthy mongrel dogs anaesthetized with pentobarbital and intubated. After 30 min. Ringer aerosol, tracheal mucus velocity (TMV by charcoal particle transport) and potential difference (PD by agar bridge) were measured under bronchoscopic control, and mucus for viscoelasticity analysis (magnetic rheometer) was collected on the endotracheal tube. On one occasion, increasing arginine conc. were aerosolized hourly, following Ringer control. On a second occasion, the same arginine solutions were used, but with 65 mg/ml low m. w. dextran (Polydex, lot #2764) added.

Results:

Buffered L-arginine has been described as a mucolytic treatment (Solomons, Pediatrics 1971; 47:384), although its effectiveness remains uncertain. However, arginine is a precursor of nitric oxide, a critical mediator in many cellular processes including mucus secretion, and there is evidence that arginine and the related amino acid lysine can stimulate transepithelial water flux via apical chloride channels, thereby increasing airway fluid hydration. Indeed, when lysine is added to the classical mucolytic N-acetylcysteine, the mucokinetic effect is enhanced, at least in part, through stimulation of epithelial Cl transfer (Tomkiewicz, Pulm Pharm 1995;8:259). In view of these considerations, we decided to study the combination of arginine and dextran to see if the mucokinetic effect of the dextran could be enhanced by coadministration of arginine, or indeed if arginine itself had significant mucolytic activity. Compared with Ringer, the lumen-negative PD decreased progressively with increasing arginine, with or without added dextran (from $-14.3 \pm 1.4$ mV to $-20.1 \pm 3.6$ mV), TMV increased on avg., but nonsignificantly ($11.9 \pm 2.2$ to $14.7 \pm 2.9$ mm/min), while mucus rigidity (log G*) decreased for dextran treatment ($2.09 \pm 0.13$ to $1.79 \pm 0.07$) but not for arginine. Our results do not support the use of arginine as a mucolytic agent by itself, nor does addition of arginine appear to augment the mucolytic activity of dextran, at least in healthy animals. However, the decrease in PD is consistent with the stimulation of transepithelial ion flux, which suggests a potentially positive effect in terms of airway fluid hydration and arginine might have a greater effect in a model of chronic bronchitis or CF.

EXAMPLE 5

With the permission of the Health Protection Branch of the Ministry of Health and Welfare Canada, one patient with advanced CF lung disease was treated with dextran. The patient was already receiving aerosolized L-arginine and dextran was administered in L-arginine. The following formulation was used: 200 mg dextran (molecular weight range of about 360 to about 4000) per ml of L-arginine solution (50 g L-arginine HCl and 3 g arginine free base per liter water: Solomons, 1971). No adverse effect was observed with a test dose of 200 mg/ml for 30 seconds and a 0.5 g dose was administered over eight minutes by nebulizer via endotracheal tube. This initial treatment resulted in the production of copious liquid secretions and the treatment was repeated three times a day over the next two days. There was evidence of liquification of secretions with each treatment. The treatment was stopped because the patient suffered a sudden episode of pulmonary decompensation.

Sputum viscoelasticity was assessed on samples obtained before and after the treatment by magnetic rheometry. The results obtained are shown in the following Table 1.

TABLE 1

| | Date | Time | Treatment | logG*1 | tand1 | MCI | CCI | Comment |
|---|---|---|---|---|---|---|---|---|
| 1 | 97.10.17 | 20:45 | pre-dextran | 1.775 | .505 | .845 | 1.490 | very purulent sample |
| 2 | 97.10.17 | 23.15 | post-dextran | 1.650 | .360 | .980 | 2.460 | |
| 3 | 97.10.20 | 16.10 | post-dextran | 2.520 | .290 | .890 | · | |

After the first treatment, elasticity deceased modestly, while viscosity decreased more substantially, and predicted mucociliary clearability and cough clearability both increased. Two days later, after the last treatment, viscosity decreased to a normal or lower than normal value while elasticity was higher and the predicted mucociliary clearability was higher than before treatment.

We claim:

1. A method of improving mucus clearance comprising administering to the respiratory tract of a patient in need of such treatment an effective amount of dextran of effective molecular weight.

2. The method of claim 1 wherein the dextran is administered in admixture with a pharmaceutically acceptable diluent or carrier.

3. The method of claim 2 wherein the diluent is sodium chloride or Ringer solution.

4. The method of claim 1 wherein the dextran is administered to the respiratory tract topically or by aerosol.

5. The method of claim 1 wherein the dextran has a weight average molecular weight of less than 500,000.

6. The method of claim 1 wherein the dextran has a molecular weight range of about 360 to about 4000.

7. A method of treating lung disease associated with impaired mucus clearance comprising administering to the respiratory tract of a patient in need of such treatment an effective amount of dextran of effective molecular weight.

8. The method of claim 7 wherein the lung disease is cystic fibrosis, chronic bronchitis, bronchiectasis or bronchial asthma.

9. The method of claim 8 wherein the polysaccharide is dextran.

10. A method of improving mucus clearability in a patient having cystic fibrosis comprising administering to the respiratory tract of a patient in need of such treatment an effective amount of dextran of effective molecular weight.

11. The method of claim 1 further comprising the step of assessing liquification of secretions of said patient following the treatment.

12. The method of claim 1 further comprising the step of assessing viscosity and elasticity of sputum of said patient following the treatment.

13. The method of claim 5 wherein the dextran has a weight average molecular weight of less than 250,000.

14. The method of claim 1 wherein the dextran has a molecular weight in the range of 4,000 or less.

15. A method of improving mucus clearance comprising administering to the respiratory tract of a patient in need of such treatment an effective amount of dextran having a molecular weight of from about 360 to about 4000.

16. The method according to claim 15, wherein the dextran is present in the respiratory secretion at a concentration of about 4 mg/ml to about 40 mg/ml.

17. A method of treating lung disease associated with impaired mucus clearance comprising administering to the respiratory tract of a patient in need of such treatment an effective amount of dextran having a molecular weight of from about 360 to about 4000.

18. The method according to claim 17, wherein the dextran is present in the respiratory secretion at concentration of about 4 mg/ml to about 40 mg/ml.

19. A method of improving mucus clearability in a patient having cystic fibrosis comprising administering to the respiratory tract of a patient in need of such treatment an effective amount of dextran having a molecular weight of from about 360 to about 4000.

20. The method according to claim 19, wherein the dextran is present in the respiratory secretion at a concentration of about 4 mg/ml to about 40 mg/ml.

21. The method according to claim 1, wherein the dextran is present in the respiratory secretion at a concentration of about 4 mg/ml to about 40 mg/ml.

22. The method according to claim 7, wherein the dextran is present in the respiratory secretion at a concentration of about 4 mg/ml to about 40 mg/ml.

23. The method according to claim 10, wherein the dextran is present in the respiratory secretion at a concentration of about 4 mg/ml to about 40 mg/ml.

* * * * *